(12) United States Patent
Nightingale

(10) Patent No.: US 11,090,206 B2
(45) Date of Patent: Aug. 17, 2021

(54) SYSTEMS AND METHODS FOR MAINTAINING A SUPPLY OF A HEALTH-RELATED ITEM

(71) Applicant: Charles Hooshmand Nightingale, St. Petersburg, FL (US)

(72) Inventor: Charles Hooshmand Nightingale, St. Petersburg, FL (US)

(73) Assignee: DIRECT PHARMS, INC., St. Petersburg, FL (US)

( * ) Notice: Subject to any disclaimer, the term of this patent is extended or adjusted under 35 U.S.C. 154(b) by 0 days.

(21) Appl. No.: 16/640,212

(22) PCT Filed: Aug. 23, 2018

(86) PCT No.: PCT/US2018/047784
§ 371 (c)(1),
(2) Date: Feb. 19, 2020

(87) PCT Pub. No.: WO2019/040770
PCT Pub. Date: Feb. 28, 2019

(65) Prior Publication Data
US 2020/0360202 A1 Nov. 19, 2020

Related U.S. Application Data

(60) Provisional application No. 62/549,317, filed on Aug. 23, 2017.

(51) Int. Cl.
*A61F 17/00* (2006.01)
*G16H 40/20* (2018.01)
(Continued)

(52) U.S. Cl.
CPC ............ *A61F 17/00* (2013.01); *G06F 16/909* (2019.01); *G06K 7/10297* (2013.01);
(Continued)

(58) Field of Classification Search
CPC ...................................................... A61F 17/00
See application file for complete search history.

(56) References Cited

U.S. PATENT DOCUMENTS 4,737,910 A * 4/1988 Kimbrow ............... G16H 40/20
705/28
2008/0004908 A1 1/2008 Oh et al.
(Continued)

OTHER PUBLICATIONS

International Search Report and Written Opinion of International patent application No. PCT/2018/047784 completed on Nov. 28, 2018. (10 pages).

*Primary Examiner* — Joseph H Feild
*Assistant Examiner* — Pameshanand Mahase
(74) *Attorney, Agent, or Firm* — Umberg Zipser LLP

(57) ABSTRACT

System and methods for maintaining a supply of health-related items are provided herein. The system includes, but is not limited to, a carrier configured to contain the health-related item. The system further includes, but is not limited to, a container having a compartment configured to store the carrier. The system includes, but is not limited to, an item presence sensor coupled to the container. The system includes, but is not limited to, a sensor tag coupled to carrier and configured to be communicatively coupled with the item presence sensor. The system includes, but is not limited to, one or more data processors configured to be communicatively coupled with the item presence sensor and configured to determine whether the health-related item is present within the container based upon proximity of the sensor tag to the item presence sensor.

3 Claims, 12 Drawing Sheets

(51) Int. Cl.
*G06F 16/909* (2019.01)
*B60R 25/24* (2013.01)
*G06K 7/10* (2006.01)
*G06K 19/07* (2006.01)

(52) U.S. Cl.
CPC ..... *G06K 7/10366* (2013.01); *G06K 19/0723* (2013.01); *G16H 40/20* (2018.01)

(56) References Cited

U.S. PATENT DOCUMENTS

| | | | |
|---|---|---|---|
| 2010/0089786 A1* | 4/2010 | Chang | B65D 5/4212 206/459.1 |
| 2011/0307284 A1* | 12/2011 | Thompson | G06Q 10/10 705/7.13 |
| 2012/0312812 A1* | 12/2012 | Sosnovsky | B65D 45/22 220/23.83 |
| 2013/0220850 A1 | 8/2013 | Wingate, III | |
| 2015/0332209 A1* | 11/2015 | DeBusk | G06Q 10/10 705/2 |
| 2016/0346056 A1* | 12/2016 | Demers | A61M 16/0051 |
| 2016/0379022 A1* | 12/2016 | Elizondo, II | G08B 13/14 340/10.1 |
| 2017/0140331 A1* | 5/2017 | Rinzler | H02J 50/80 |
| 2018/0096292 A1* | 4/2018 | DeBusk | G06Q 10/087 |

* cited by examiner

SYSTEMS AND METHODS FOR MAINTAINING A SUPPLY OF A HEALTH-RELATED ITEM

CROSS-REFERENCE TO RELATED APPLICATIONS

This application claims the benefit of U.S. Provisional Application No. 62/549,317, filed Aug. 23, 2017.

TECHNICAL FIELD

The technical field is directed to a system and a method for maintaining a supply of a health-related item.

BACKGROUND

Healthcare costs are increasing at an uncontrolled rate. Many of these cost increases are due to patients unnecessarily utilizing the emergency department for conditions that can be reasonably treated, or at minimum, stabilized outside the hospital and thus allow the patient to schedule an appointment with their primary care physician. One barrier preventing the treatment or stabilizing of the conditions outside the hospital is access to the medications, devices, and supplies commonly utilized to treat or stabilized the conditions. While the medications, devices, and supplies are likely available at a local store, a patient's stock of these health-related items at home or office may be limited, expired, or recalled without the patient knowing until the need arises. In many cases, the patient will go to the emergency department rather than attempt to find an item suitable to treat or stabilize the condition.

While it is important for patients to utilize these health-related items when appropriate, healthcare professionals are not typically in a position to monitor usage of these items outside of the hospital/clinical environment. Monitoring usage can provide useful information to the patient, patient's family, primary healthcare provider, or other healthcare professional.

As such, it is desirable to provide a system and a method for maintaining a supply of a health-related item. In addition, other desirable features and characteristics will become apparent from the subsequent summary and detailed description, and the appended claims, taken in conjunction with the accompanying drawings and this background.

SUMMARY

A system for maintaining a supply of a health-related item is provided herein. The system includes, but is not limited to, a carrier configured to contain the health-related item. The system further includes, but is not limited to, a container having a compartment configured to store the carrier. The system includes, but is not limited to, an item presence sensor coupled to the container. The system includes, but is not limited to, a sensor tag coupled to carrier and configured to be communicatively coupled with the item presence sensor. The system includes, but is not limited to, one or more data processors configured to be communicatively coupled with the item presence sensor and configured to determine whether the health-related item is present within the container based upon proximity of the sensor tag to the item presence sensor.

A processor-implemented system for maintaining a supply of a health-related item is also provided herein. The system includes, but is not limited to, a storage device for storing instructions for maintaining the supply of the health-related item. The system further includes, but is not limited to, one or more data processors configured to execute the instructions to receive, by one or more data processors, presence data of the health-related item from a storage space, the storage space comprises an item presence sensor configured to determine whether the health-related item is present within the storage space, receive, by one or more data processors, status data of the health-related item from a database, access, by one or more data processors, a reorder model that generates a reorder signal in response to the presence data and the status data, the reorder model comprises a pre-specified reorder threshold, and generate the reorder signal upon satisfying the pre-specified reorder threshold.

Another processor-implemented system for maintaining a supply of a health-related item is also provided herein. The system includes, but is not limited to, a storage device for storing instructions for maintaining the supply of the health-related item. The system further includes, but is not limited to, one or more data processors configured to execute the instructions to receive, by one or more data processors, presence data of the health-related item from a storage space, the storage space comprises an item presence sensor configured to determine whether the health-related item is present in the storage space, receive, by one or more data processors, geographic location data of the storage space from a database, access, by one or more data processors, a tracking model that generates an elevated-usage signal in response to the presence data and the geographic location data, the model comprises a pre-specified usage threshold, and generate the elevated-usage signal upon satisfying the pre-specified usage threshold.

BRIEF DESCRIPTION OF THE DRAWINGS

Other advantages of the disclosed subject matter will be readily appreciated, as the same becomes better understood by reference to the following detailed description when considered in connection with the accompanying drawings wherein.

DETAILED DESCRIPTION

Figure 1:
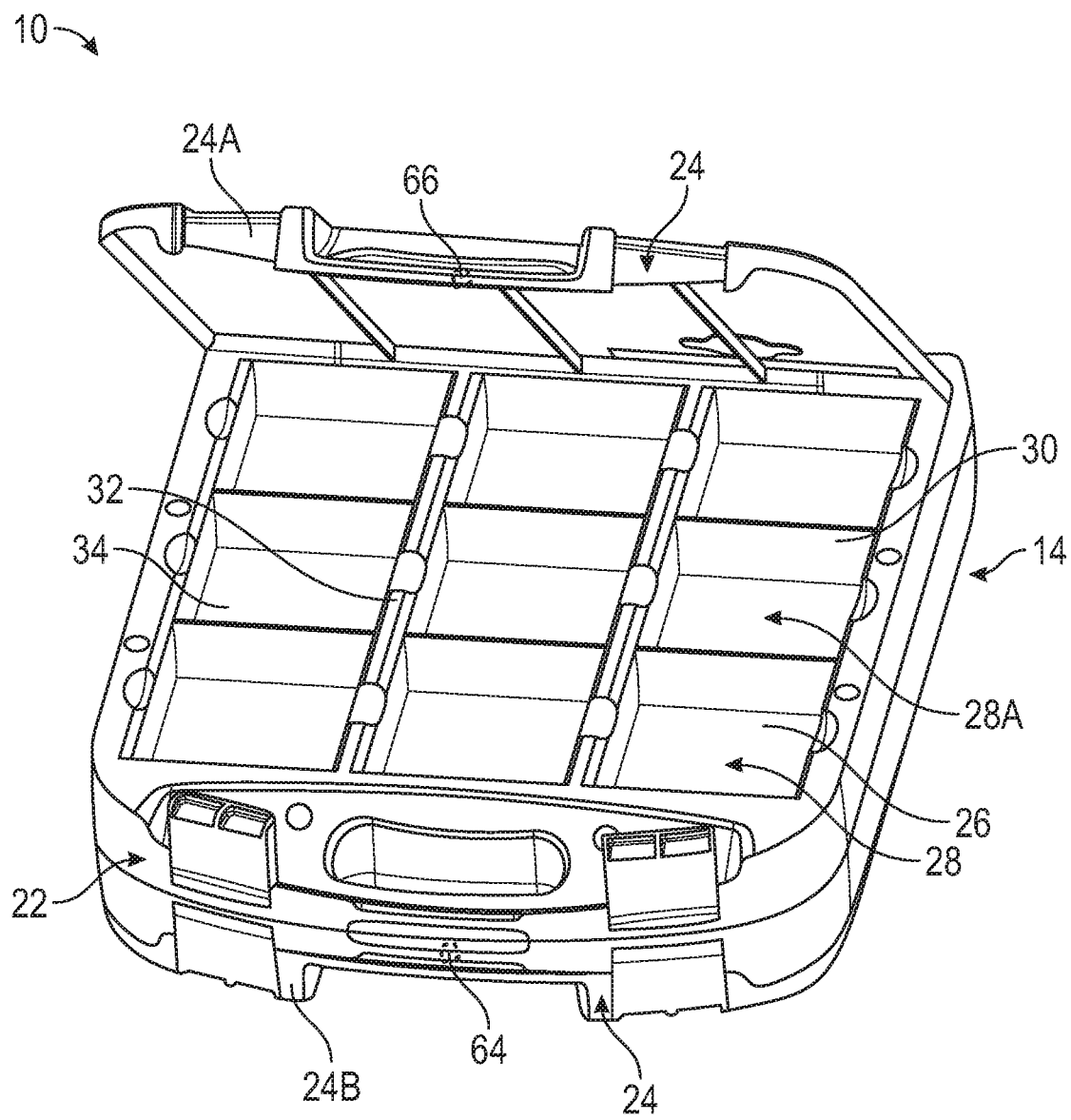
FIG. 1 is a perspective view illustrating a non-limiting embodiment of a system for maintaining a supply of health-related items including a container.

The following detailed description is merely exemplary in nature and is not intended to limit the invention or the application and uses of the invention. Furthermore, there is no intention to be bound by any theory presented in the preceding background or the following detailed description. It should be understood that throughout the drawings, corresponding reference numerals indicate like or corresponding parts and features.

The features and advantages identified in the present disclosure will be more readily understood, by those of ordinary skill in the art, from reading the following detailed description. It is to be appreciated that certain features, which are, for clarity, described above and below in the context of separate embodiments, may also be provided in combination in a single embodiment. Conversely, various features that are, for brevity, described in the context of a single embodiment, may also be provided separately or in any sub-combination. In addition, references in the singular may also include the plural (for example, "a" and "an" may refer to one, or one or more) unless the context specifically states otherwise.

The use of numerical values in the various ranges specified in this disclosure, unless expressly indicated otherwise, are stated as approximations as though the minimum and maximum values within the stated ranges were both proceeded by the word "about." In this manner, slight variations above and below the stated ranges can be used to achieve substantially the same results as values within the ranges. Also, the disclosure of these ranges is intended as a continuous range including every value between the minimum and maximum values.

Techniques and technologies may be described herein in terms of functional and/or logical block components, and with reference to symbolic representations of operations, processing tasks, and functions that may be performed by various computing components or devices. It should be appreciated that the various block components shown in the figures may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

The following description may refer to elements or nodes or features being "coupled" together. As used herein, unless expressly stated otherwise, "coupled" means that one element/node/feature is directly or indirectly joined to (or directly or indirectly communicates with) another element/node/feature, and not necessarily mechanically. Thus, although the drawings may depict one exemplary arrangement of elements, additional intervening elements, devices, features, or components may be present in an embodiment of the depicted subject matter. In addition, certain terminology may also be used in the following description for the purpose of reference only, and thus are not intended to be limiting.

Techniques and technologies may be described herein in terms of functional and/or logical block components and with reference to symbolic representations of operations, processing tasks, and functions that may be performed by various computing components or devices. Such operations, tasks, and functions are sometimes referred to as being computer-executed, computerized, software-implemented, or computer-implemented. In practice, one or more processor devices can carry out the described operations, tasks, and functions by manipulating electrical signals representing data bits at memory locations in the system memory, as well as other processing of signals. The memory locations where data bits are maintained are physical locations that have particular electrical, magnetic, optical, or organic properties corresponding to the data bits. It should be appreciated that the various block components shown in the figures may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

For the sake of brevity, conventional techniques related to graphics and image processing, touchscreen displays, and other functional aspects of certain systems and subsystems (and the individual operating components thereof) may not be described in detail herein. Furthermore, the connecting lines shown in the various figures contained herein are intended to represent exemplary functional relationships and/or physical couplings between the various elements. It should be noted that many alternative or additional functional relationships or physical connections may be present in an embodiment of the subject matter.

As used herein, the term "module" refers to any hardware, software, firmware, electronic control component, processing logic, and/or processor device, individually or in any combination, including without limitation: application specific integrated circuit (ASIC), an electronic circuit, a processor (shared, dedicated, or group) and memory that executes one or more software or firmware programs, a combinational logic circuit, and/or other suitable components that provide the described functionality.

A system 10 (or processor-implemented system 10) for maintaining a supply of a health-related item 12 is provided herein with reference to FIGS. 1-3 and 12. The system 10 includes a carrier 46 configured to contain the health-related item 12. The system 10 further includes a container 14 having a compartment 28 configured to store the carrier 46. The system 10 further includes an item presence sensor 16 coupled to the container 14. The system 10 further includes a sensor tag 18 coupled to carrier 46 and configured to be communicatively coupled with the item presence sensor 16. The system 10 further includes one or more data processors 20 configured to be communicatively coupled with the item presence sensor 16 and configured to determine whether the health-related item 12 is present within the container 14 based upon proximity of the sensor tag 18 to the item presence sensor 16. By determining whether the health-related item 12 is present within the container 14, an exhausted supply of the health-related item 12 may be automatically reordered, when appropriate, and a user of the system 10 may obtain information and statistics relating to usage of the health-related item 12. Information may include allergy information, potential negative interactions between medications, recommendations regarding scheduling appointments with a healthcare professional, usage by a family member or a dependent, communication with healthcare providers regarding usage, etc. Statistics may include elevated-usage statistics of certain health-related items 12 or certain classes of health-related items 12 based on geographical location, age, gender, ethnicity, profession, environment, lifestyle, etc.

The health-related item 12 may include over-the-counter (OTC) medications, prescription medications, bandages, sterilizing solutions, lotions, creams, sprays, medical devices, or combinations thereof. Non-limiting examples of suitable health-related items 12 include items having trade names or common names, such as Tylenol, Motrin, Naprosyn, Aspirin, Benadryl, Claritin, Hydrocortisone cream, Cough drops, Vitamin C, Mucinex, Sudafed, Flonase, Airborne, Orajel, Pepto, Gas-X, Tums, Ducolax, Imodium, Pepcid, Bandages, Neosporin, Sanitizing Wipes, Diaper Cream, Saline Nasal Spray, Thermometer, Suture Kit, Aspirator, and the like. It is to be appreciated that any of the items identified by their trade names may also be included as a generic item. In various embodiments, the system 10 includes a plurality of health-related items 12 that may be the same or different.

Figure 12A:
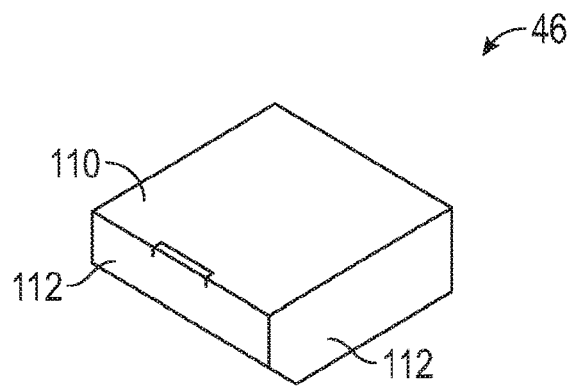
FIGS. 12A, 12B, and 12C are perspective views illustrating non-limiting embodiments of a carrier of the system of FIG. 1.
Figure 12B:
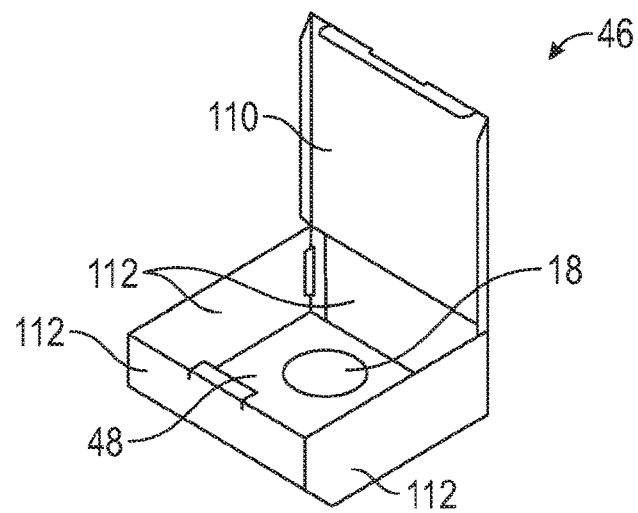
Figure 12C:
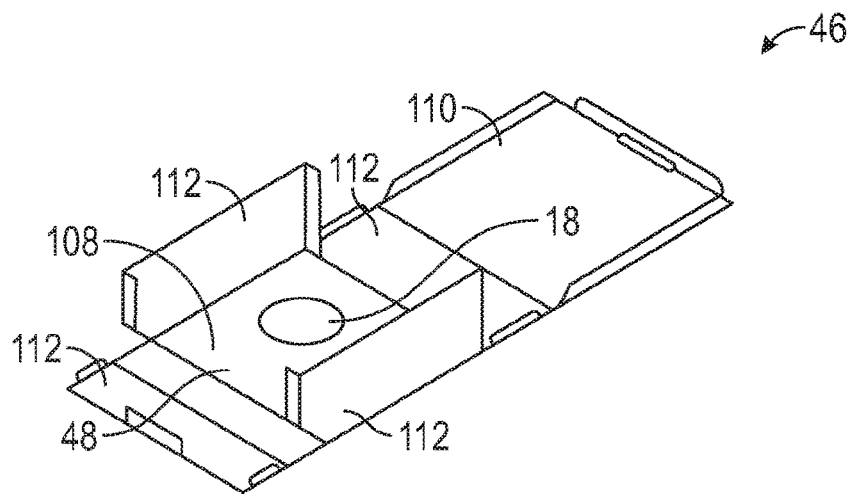

With particular reference to FIGS. 12A, 12B, and 12C, as introduced above, the system 10 may include the carrier 46 configured to contain the health-related item 12. The carrier 46 may be formed from a polymeric material, such as a thermoplastic material. However, it is to be appreciated that the container 14 may be formed from non-polymeric materials, such as glass-containing materials, ceramic-containing materials, metal-containing materials, and the like. In certain embodiments, the carrier 46 defines a pocket 48, and the health-related item 12 is disposed within the pocket 48. The carrier 46 may be translucent to permit visibility of the health-related item 12 disposed within the pocket 48. It is to be appreciated that only a portion of the health-related item 12 may be disposed within the pocket 48 for the health-related item 12 to be considered disposed within the pocket 48.

The carrier 46 may be configured to dimensionally cooperate with the compartment 28 such that undesired movement of the carrier 46 relative to the compartment 28 is minimized. The pocket 48 may be configured to dimensionally cooperate with the health-related item 12 such that movement of the health-related item 12 relative to the carrier 46 is minimized. In certain embodiments, the system 10 includes a plurality of carriers 46 configured to contain the plurality of health-related items 12. It is to be appreciated that when the system 10 includes the plurality of health-related items 12, one of the carriers 46 may be configured to dimensionally cooperate with one or more of the same health-related item 12 and another one of the carriers 46 may be configured to dimensionally cooperate with one or more of a different health-related item 12. For example, one of the carriers 46 may be configured to dimensionally cooperate with twenty bandages and another one of the carriers 46 may be configured to dimensionally cooperate with six two-packs of ibuprofen. Non-limiting examples of suitable carriers 46 include boxes, sleeves, blister packs, bottles, caddies, casings, packages, syringes, wrappers, bags, and the like.

In certain embodiments, the carrier 46 includes a base 108 and a cover 110 opposite the base 108. The carrier 46 further includes two or more sides 112, such as four sides 112, disposed between the base 108 and the cover 110. The pocket 48 is defined between the base 108, the cover 110, and the sides 112. As will be described in greater detail below, the sensor tag 18 may be couple to the carrier 46, such as coupled to the base 108 within the packet 48. However, it is to be appreciated that the sensor tag 18 may be coupled to any portion of the carrier 46.

The container 14 may be formed from a polymeric material. However, it is to be appreciated that the container 14 may be formed from non-polymeric materials, such as glass-containing materials, ceramic-containing materials, metal-containing materials, and the like. The container 14 may include a housing 22 and one or more covers 24 pivotably coupled to the housing 22. However, it is to be appreciated that the cover 24 may be coupled to the housing 22 in any manner known in the art, such as slidably coupled, rotatably coupled, coupled via friction or interlocking components, and the like. In certain embodiments, the container 14 includes a first cover 24A and a second cover 24B with the first cover 24A and the second cover 24B opposite each other relative to the housing 22. The container 14 may further include one or more latches for securing the cover 24 to the housing 22. Alternative to the container 14, the system 10 may include a storage space. In various embodiments, the storage space may be any space configured to store the health-related items 12 that is defined by "fencing" the health-related items 12 to a predetermined area utilizing the item presence sensor 16. Non-limiting examples of suitable storage spaces may include shelves, closets, bags, containers, vehicles, boxes, rooms, etc. The storage space may include the container 14.

The housing 22 may define one or more cavities 26 configured to receive the health-related items 12. The housing 22 may include one or more spacers 30 configured to cooperate with the housing 22 and the one or more cavities 26 for forming the compartment 28 within the cavity 26. The housing 22 may include a plurality of compartments 28 configured to store the plurality of carriers 46. The size and orientation of the compartments 28 may be adjustable relative to each other such that health-related items 12 having various configurations and sizes may be received by the compartments 28 and sufficiently supported by the housing 22. However, it is to be appreciated that the item presence sensor 16 must be sufficiently aligned relative to each of the compartments 28 for determining whether the health-related item 12 has been displaced from the container 14. In various embodiments, the housing 22 includes a first compartment 28A facing the first cover 24A and a second compartment 28B facing the second cover 24B.

As introduced above, the system 10 further includes the item presence sensor 16 coupled to the container 14. In embodiments, the item presence sensor 16 is disposed within the container 14 and configured to determine whether one or more of the health-related items 12 has been displaced from the container 14. Non-limiting examples of suitable item presence sensors 16 include light sensors (e.g., visible light sensors, infrared light sensors, and ultraviolet light sensors), electromagnetic field sensors (e.g., Radio-frequency identification (RFID) or RFID/near-field communication (NFC)), pressure sensors, ultrasonic sensors, capacitive sensors, inductive sensors, and combinations thereof.

In certain embodiments, the item presence sensor 16 is an RFID/NFC sensor. In embodiments wherein the item presence sensor 16 is an RFID/NFC sensor, the item presence sensor 16 includes an antenna and a sensor controller. Non-limiting examples of suitable sensor controllers include NFC/RFID controller breakout boards, such as the NFC/RFID controller breakout board commercially available from Adafruit Industries of New York City, N.Y. under the tradename PN532.

Figure 2:
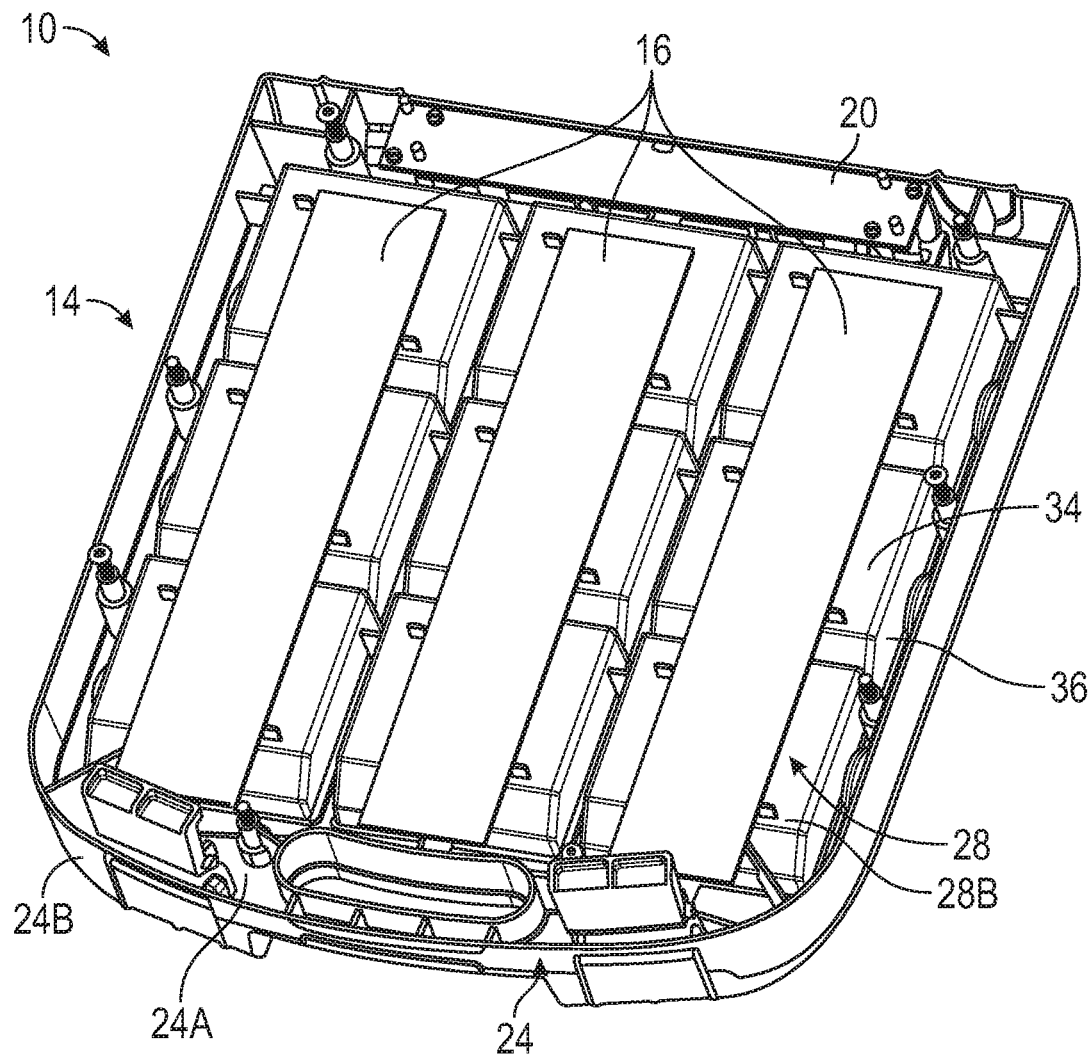
FIG. 2 is another perspective view illustrating a non-limiting embodiment of the system of FIG. 1.

With particular reference to FIG. 2, the system 10 may include more than one item presence sensor 16 disposed within the container 14 with each of the item presence sensors 16 disposed adjacent one of the compartments 28 of the housing 22. In an exemplary embodiment, the housing 22 includes eighteen compartments 28 with one of the item presence sensors 16 disposed adjacent each of the compartments 28 such that the system 10 includes eighteen item presence sensors 16. In an exemplary embodiment, nine of the item presence sensors 16 are oriented in a 3×3 array with the system 10 including two 3×3 arrays disposed adjacent the compartments 28. In an exemplary embodiment, the item presence sensor 16 may be disposed between the first compartment 28A and the second compartment 28B.

Referring back to FIGS. 1-3, the item presence sensor 16 may be disposed adjacent a side portion 32 of the compartment 28, the base portion 34 of the compartment 28, or a combination thereof. Selection of either the side portion 32 or the base portion 34 for location of the item presence sensor 16 may be dependent on the type of health-related item 12 included in the compartment 28. For example, detection by the item presence sensor 16 of health-related items 12 including a metal-containing backing, such as a wipe packet, may be improved by placing the item presence sensor 16 adjacent the side portion 32 of the compartment 28. This placement of the item presence sensor 16 may reduce interference caused by the metal-containing backing. In one embodiment, the item presence sensor 16 is disposed adjacent the base portion 34 of the compartment 28. In another embodiment, the item presence sensor 16 is disposed adjacent the side portion 32 of the compartment 28. The item presence sensor 16 may have a detection range of from about 1 centimeter (cm) to about 50 cm, alternatively from about 1 cm to about 10 cm, or alternatively from about 2 cm to about 8 cm.

As introduced above, the system 10 may further include the sensor tag 18 coupled to each of the health-related items 12. The sensor tag 18 may be directly or indirectly coupled to the health-related items 12 utilizing an adhesive, a fastener, stitching, or combinations thereof. In certain embodiments, the sensor tag 18 is coupled to the carrier 46 and thus the sensor tag 18 is indirectly coupled to the health-related item 12, when present. The sensor tag 18 is configured to be communicatively coupled with the item presence sensor 16. The sensor tag 18 may be passive or active. In embodiments wherein the item presence sensor 16 is an RFID/NFC sensor, the sensor tag 18 may be an RFID tag including a unique identification (UID). In certain embodiments, the system 10 includes a plurality of sensor tags 18 with each of the carriers 46 including one of the plurality of sensor tags 18. Each of the plurality of sensor tags 18 has a unique identification and thus each of the health-related items 12 may correspond with have a particular UID different from the other health-related items 12. The RFID/NFC sensor may be passively energized by radio waves generated by the item presence sensor 16. In an exemplary embodiment, the RFID tag is a metal-type RFID tag which exhibits improved detection by the item presence sensor 16 in the presence of various materials, such as metal foils. Other non-limiting examples of the sensor tag 18 may include a contact-based integrated circuit, such as a microchip. The contact-based integrated circuit may be configured to cooperate with the item presence sensor 16. The item presence sensor 16 may be in electrical communication with the contact-based integrated circuit of the sensor tag 18 when the health-related item 12 is present in the container 14.

As introduced above, the system 10 further includes one or more data processors 20 configured to be communicatively coupled with the item presence sensor 16. The one or more data processors 20 can be any custom made or commercially available processor, a central processing unit (CPU), an auxiliary processor among several processors associated with the container 14, a semiconductor based microprocessor (in the form of a microchip or chip set), a macroprocessor, or generally any device for executing instructions. The one or more data processors 20 may be communicatively coupled with any component of the system 10 through wired connections, wireless connections and/or devices, or a combination thereof. Examples of suitable wired connections includes, but are not limited to, hardware couplings, splitters, connectors, cables or wires. Examples of suitable wireless connections and devices include, but not limited to, Wi-Fi device, Bluetooth device, wide area network (WAN) wireless device, Wi-Max device, local area network (LAN) device, 3G/4G/5G broadband device, GSM/CDMA cellular networks, infrared communication device, optical data transfer device, radio transmitter and optionally receiver, wireless phone, wireless phone adaptor card, or any other devices that can transmit signals in a wide range of electromagnetic wavelengths including radio frequency, microwave frequency, visible or invisible wavelengths.

The system 10 may be centralized or decentralized. In certain embodiments, the system 10 may further include a server 36. The server 36 may be located distant from the container 14 and communicatively coupled to the container 14, as described above. The system 10 or the server 36 may include a cloud computing environment for communicatively coupling the server 10 and the container 14. In other embodiments, the system 10 may be decentralized and operate on a peer-to-peer network whereby the various data generated by the system 10 is contained on a blockchain. In this decentralized embodiment, the system 10 includes various nodes, such as user nodes which may include the container 14 and logistics nodes for managing ordering, delivery, and status updates of the health-related items 12. It is to be appreciated that the system 10 may utilize a combination of centralized and decentralized operations.

With reference to FIGS. 3-7, the system 10 may be configured to determine, by the one or more data processors 20, whether one or more of the health-related items 12 is present within the container 14 based upon the proximity of the sensor tag 18 to the item presence sensor 16 utilizing a displacement model 50. The displacement model 50 may be an algorithm configured to determine when one or more of the health-related items 12 have been displaced from the container 14 or whether one or more of the health-related items 12 are present within the container 14. In certain embodiments, the determination of whether one or more of the health-related items 12 have been displaced from the container 14 or whether one or more of the health-related items 12 are present within the container 14 is based upon whether the item presence sensor 16 detects the sensor tag 18. In various embodiments, the item presence sensor 16 is configured to generate an inquiry signal, and the sensor tag 18 is configured to generate a feedback signal in response to the inquiry signal when the carrier 46 is stored in the container 14. The one or more data processors 20 may be further configured to generate presence data for each of the health-related items 12 based upon whether the item presence sensor 16 detects the sensor tag 18 corresponding to the health-related item 12. The presence data may be utilized to generate a graphical user interface 62 (e.g., a dashboard 62A, an inventory list 62B, or a product information page 62C) of the presence of the health-related items 12.

In various embodiments, the sensor tag 18 is in proximity of the item presence sensor 16 when the sensor tag 18 is within a detection range of the item presence sensor 16 of from about 1 centimeter (cm) to about 50 cm, alternatively from about 1 cm to about 10 cm, or alternatively from about 2 cm to about 8 cm. Alternatively, in embodiments when the sensor tag 18 includes the contact-based integrated circuit, the sensor tag 18 is in proximity of the item presence sensor 16 when the contact-based integrated circuit is in direct electrical communication with the presence sensor 16. It is to be appreciated that the sensor tag 18 may be in proximity of the item presence sensor 16 utilizing direct electrical communication (e.g., contact-based integrated circuit), indirect electrical communication, visual-based identification (e.g., barcode and matrix barcode), infrared-based identification (e.g., IRID), emission spectra identification, or combinations thereof.

In certain embodiment, the systems 10 is configured to initiate detection of the sensor tag 18 by the item presence sensor 16 at pre-specified intervals of time. The pre-specified intervals of time may extend from about 1 second to about 240 hours, alternatively from about 1 minute to about 12 hours, alternatively from about 10 minutes to about 6 hours, or alternatively from about 4 hours to about 6 hours. In an exemplary embodiment, the system 10 is configured to generate an initiation signal at pre-specified intervals of time, and the item presence sensor 16 is configured to generate an inquiry signal in response to the initiation signal. In certain embodiment, the system 10 is configured to initiate detection of the sensor tag 18 by the item presence sensor 16 when the cover 24 is moved from an open position to a closed position, or from a closed position to an open position, relative to the housing 22. In an exemplary embodiment, the housing 22 includes a door sensor 64, the cover 24 includes a magnet 66 configured to cooperate with the door sensor 64, the door sensor 64 is configured to generate an initiation signal in response to separation of the magnet 66 and the door sensor 64, and the item presence sensor 16 is configured to generate an inquiry signal in response to the initiation signal.

Figure 3:
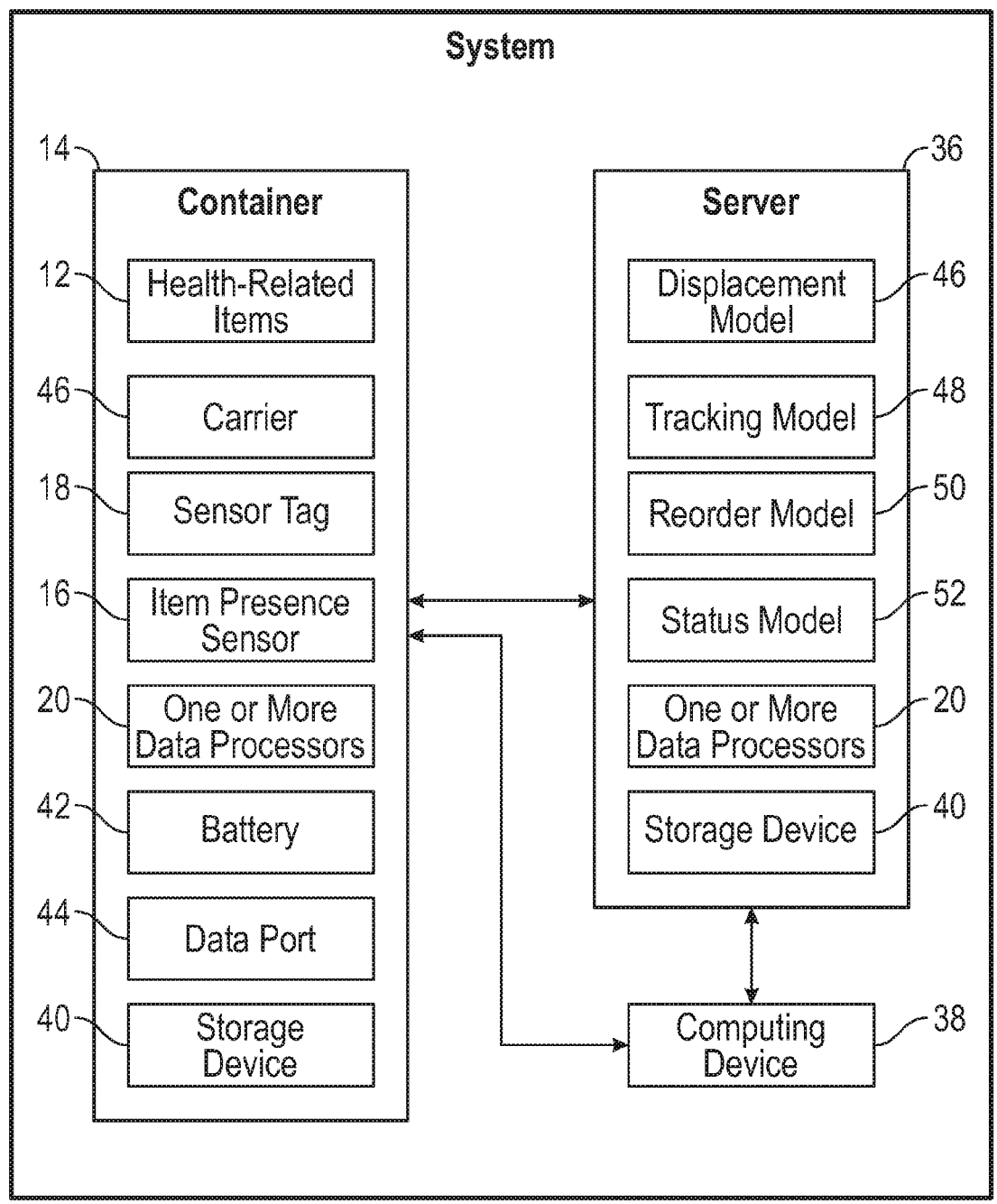
FIG. 3 is a flow chart illustrating a non-limiting embodiment of the system of FIG. 1.
Figure 4:
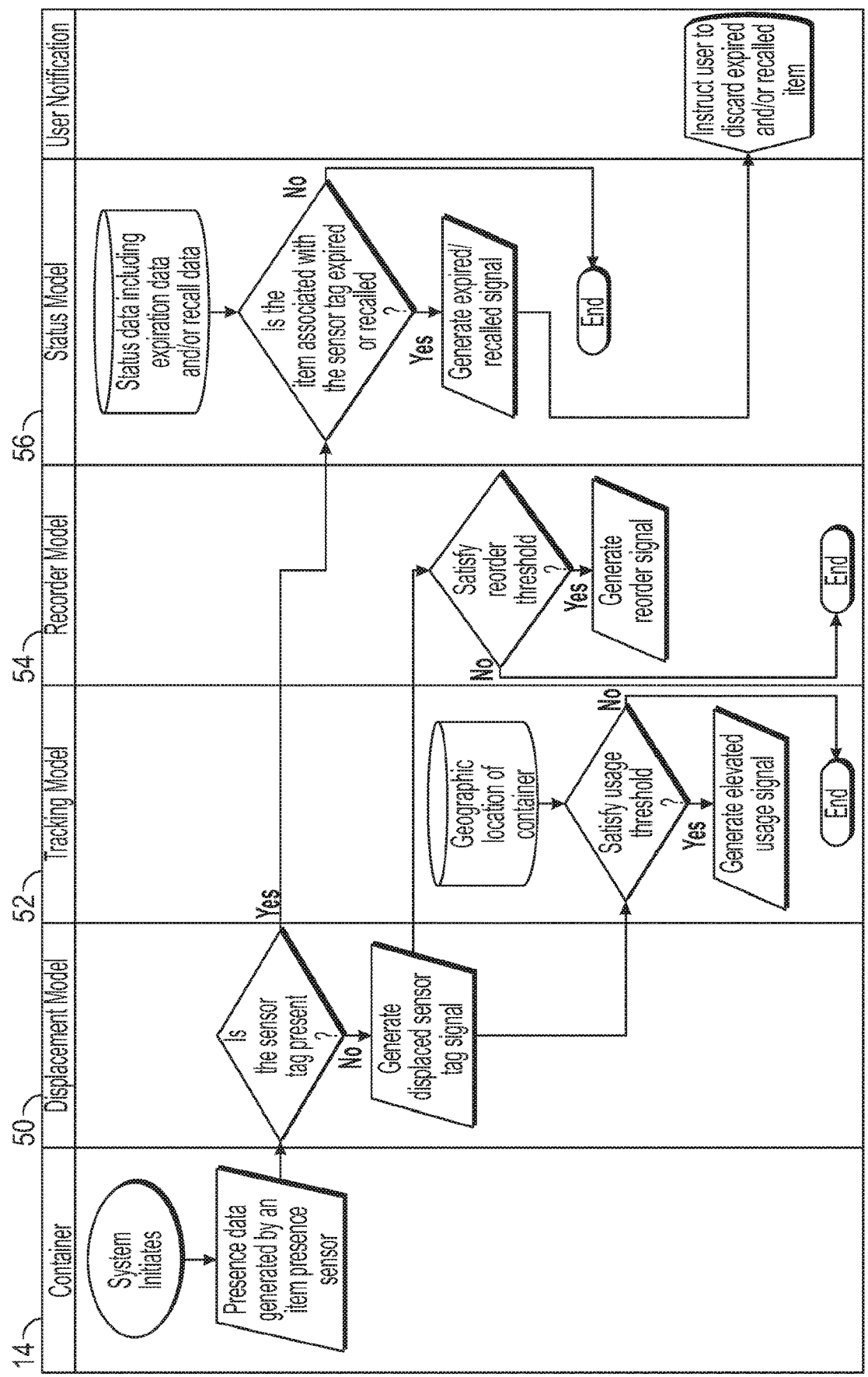
FIG. 4 is another flow chart illustrating a non-limiting embodiment of the system of FIG. 1.
Figure 5:
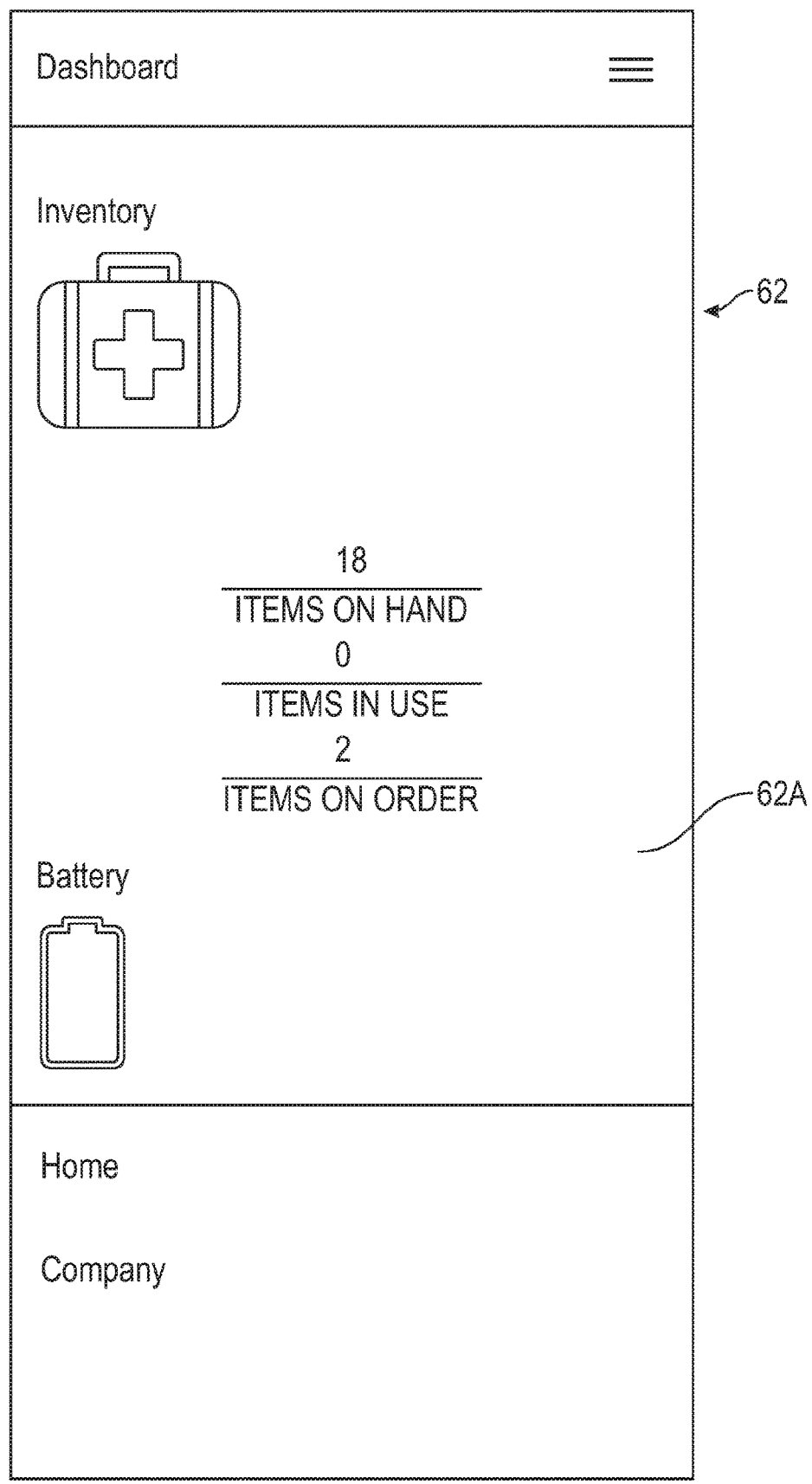
FIG. 5 is an image illustrating a non-limiting embodiment of a graphical user interface of the system of FIG. 1.
Figure 6:
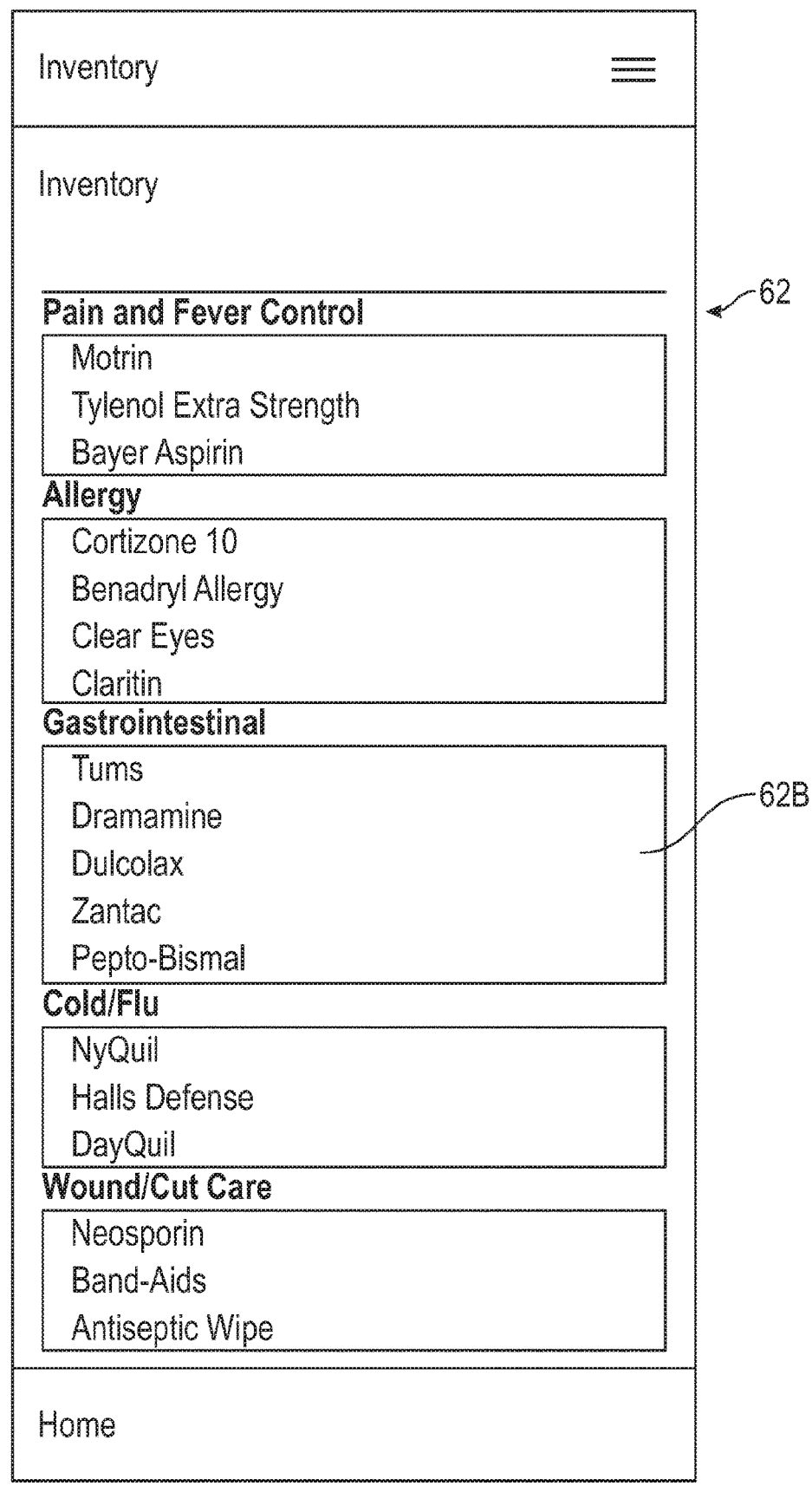
FIG. 6 is an image illustrating a non-limiting embodiment of another graphical user interface of the system of FIG. 1.
Figure 7:
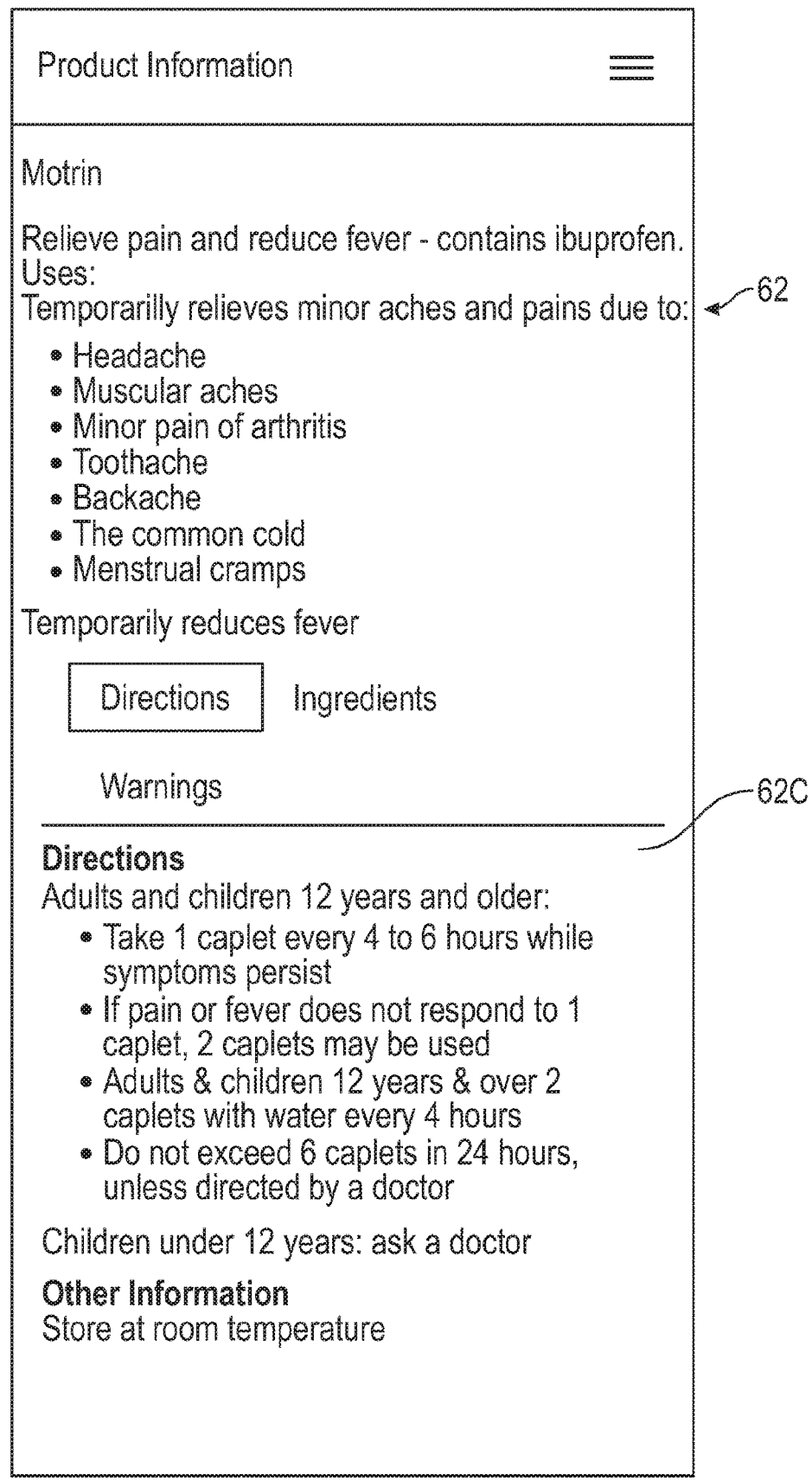
FIG. 7 is an image illustrating a non-limiting embodiment of another graphical user interface of the system of FIG. 1.
Figure 8:
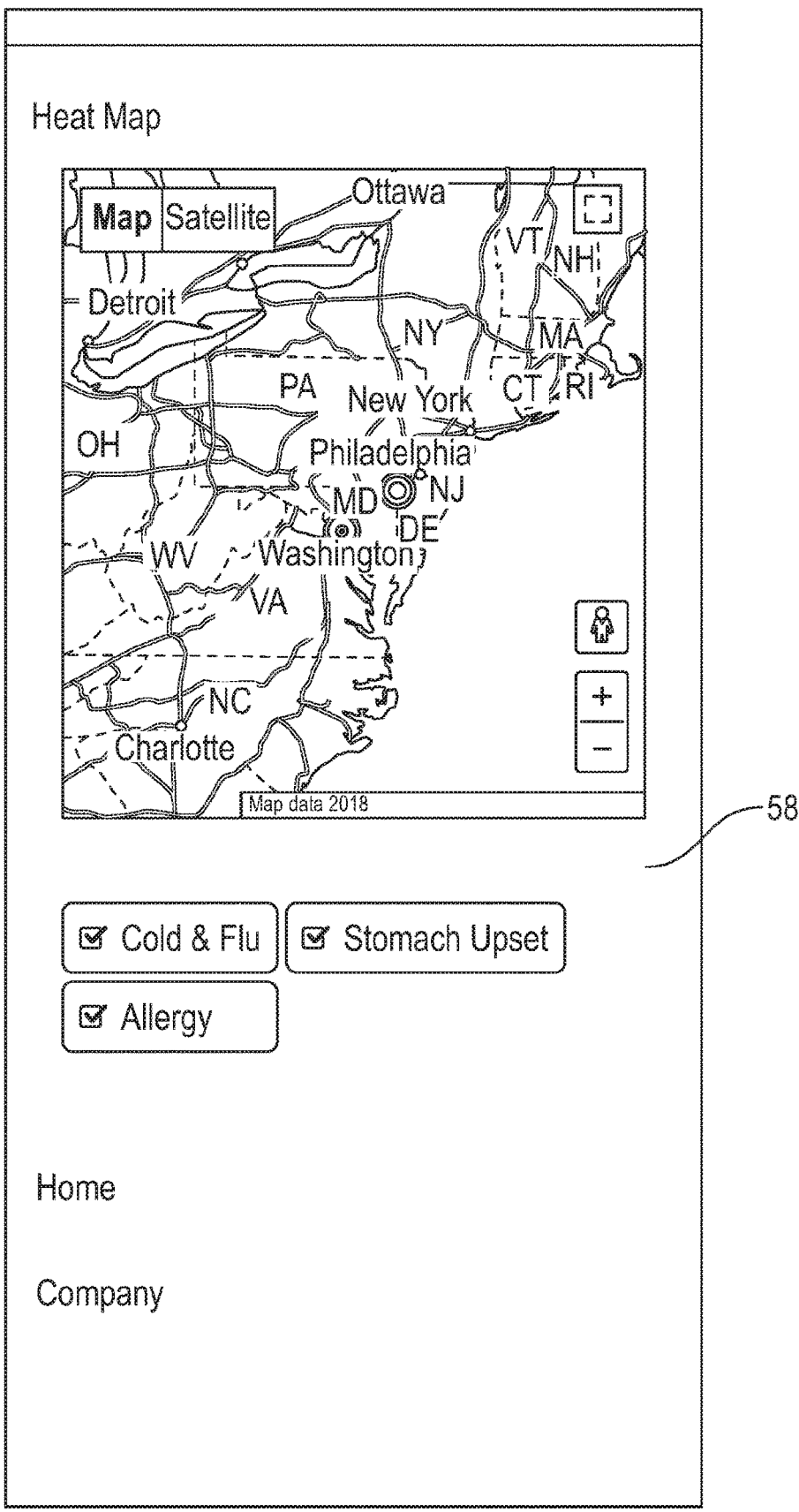
FIG. 8 is an image illustrating a non-limiting embodiment of a graphical analysis of the system of FIG. 1.

With reference to FIGS. 3, 4, and 8, the system 10 may be further configured to determine, by the one or more data processors 20, usage data of the health-related items 12 based on geographic location of the container 14 utilizing a tracking model 52. The usage data may be based on whether one or more of the health-related items 12 is present within the container 14. The tracking model 52 may be an algorithm configured to determine whether one or more of the health-related items 12 has been displaced from the container 14 in view of the geographic location of the container 14. The tracking model 52 may be utilized to determine elevated utilization of one or more of the health-related items 12 in view of the geographic location of the container 14. The determination of elevated utilization may be based on whether a pre-specified usage threshold is satisfied. The pre-specified usage threshold may be statically (e.g., fixed usage amount) or dynamically (e.g., relative to usage outside geographic location) generated.

An elevated-usage signal may be generated when the pre-specified usage threshold is satisfied. The tracking model 52 may be utilized to determine whether an elevated increase of a disease or an occurrence is present in a particular geographic location. For example, an elevation in the use of gastrointestinal medication in one state-wide geographic location relative to the use of the gastrointestinal medication in an entire country-wide geographic location may indicate the presence of food-borne pathogens in the one state-wide geographic location. The geographic location of the container 14 may be based on GPS receiver, pre-specified user information (e.g., mailing delivery address), IP address, and the like. The determination of geographic location may be based on the pre-specified intervals of time described above or when the cover 24 is moved from an open position to a closed position, or from a closed position to an open position, relative to the housing 22. The container 14 may include a unique identification (UID) for tracking the geographic location of the container 14. The usage data may be utilized to generate a graphical analysis 58 (e.g., a heat map) of the usage of the health-related items 12.

With reference to FIGS. 3 and 4, the system 10 may be further configured to determine, by the one or more data processors 20, a status of each of the health-related items 12 utilizing a status model 56. The status may include expiration information related to the health-related items 12, recall information related to the health-related items 12, or a combination thereof. The status model may be an algorithm configured to determine whether one or more of the health-related items 12 are expired or recalled. Upon determination that one or more of the health-related items 12 is expired or recalled, the one or more data processors 20 may be configured to determine whether the expired or recalled health-related item 12 is present in the container 14. In other words, the one or more data processors 20 may initiate a determination of whether one or more of the health-related items 12 is present within the container 14 is based upon whether the item presence sensor 16 detects the sensor tag 18. If the expired or recalled health-related item 12 is present in the container 14, a notification may be sent to a user to instruct the user to discard the expired and/or recalled health-related item 12. Status data, which includes the expiration information and the recall information, may be located in a status database. The status data located in the status database may correspond to the UID of the carrier 46 that contains the health-related item 12.

The system 10 may be further configured to access, by the one or more data processors 20, a reorder model 54 configured to generate a reorder signal in response to the presence data and/or the status data. In certain embodiments, the system 10 is configured to determine, by the one or more data processors 20, whether the supply of one or more of the health-related items 12 has been exhausted utilizing the reorder model 54. The reorder model may be an algorithm configured to determine whether the reorder signal is generated and thus whether one or more of the health-related items 12 may be sent to the user for restocking the container 14. The reorder model 54 includes the pre-specified reorder threshold for determining whether the reorder signal is generated. In embodiments, the reorder threshold is a pre-specified quantity or weight of the health-related items 12. The reorder model 54 may generate a reorder signal in response to the presence data upon satisfying the pre-specified reorder threshold. In an exemplary embodiment, the container 14 includes a three-day supply of the health-related items 12 such that any displacement of the health-related items 12 from the container 14 will satisfy the pre-specified reorder threshold.

The system 10 may be further configured to be utilized in a regulated environment, such as OSHA regulated environment, required to possess onsite a specific supply of health-related items 12. Non-limiting examples of suitable regulated environments includes manufacturing sites, construction sites, energy generation sites, chemical processing sites, laboratories, hospitals, restaurants, and the like. As the regulations change, the system 10 may be configured to notify the user of the change and may be configured to initiate a delivery process for sending the user a compliant supply of health-related items 12. The system 10 may be further configured to generate a usage notification in response to opening of the cover 24, displacement of one or more health-related items 12, or a combination thereof. The usage notification may be utilized for notifying a supervisor of the user that the container 14 was opened, that a specific item 12 was utilized which may relate to one or more injuries, or a combination thereof. The system 10 may be configured to generate a report including a listing of the specific item 12 that was utilized and a listing including potential injuries related to the specific item 12. The system 10 may be also configured to generate a report confirming that a compliant supply of health-related items 12 is available onsite in the regulated environment, such as an incident report. The system 10 may be actively monitored to comply with regulation of the regulated environment.

The system 10 may be further configured to determine, by the one or more data processors 20, usage data of the health-related items 12 based on a tracking model. The usage data may be based on whether one or more of the health-related items 12 is present within the container 14. The tracking model 52 may be an algorithm configured to determine whether one or more of the health-related items 12 has been displaced from the container 14. The tracking model 52 may be utilized to determine reduced utilization of one or more of the health-related items 12. The determination of reduced utilization may be based on whether a pre-specified usage threshold is satisfied. The pre-specified usage threshold may be statically (e.g., fixed usage amount) generated. A reduced-usage signal may be generated when the pre-specified usage threshold is satisfied. The tracking model may be utilized to determine whether a user's use of a certain health-related item 12 has been reduced. The system 10 may then be configured to alert a family member, guardian, or healthcare professional of the reduced usage. For example, a reduction in the use of an antipsychotic medication by a user may indicate that intervention is necessary by a family member, guardian, or healthcare professional.

The system 10 may be further configured to determine, by the one or more data processors 20, usage data of the health-related items 12 based on a tracking model. The usage data may be based on whether one or more of the health-related items 12 is present within the container 14. The tracking model 52 may be an algorithm configured to determine whether one or more of the health-related items 12 has been displaced from the container 14. The tracking model 52 may be utilized to determine unexpected/unauthorized utilization of one or more of the health-related items 12. The determination of the unexpected/unauthorized utilization may be based on whether a pre-specified usage threshold is satisfied. The pre-specified usage threshold may be statically (e.g., fixed usage amount) generated. An unexpected/unauthorized-usage signal may be generated when the pre-specified usage threshold is satisfied. The tracking model may be utilized to determine whether a user's use of a certain health-related item 12 is unexpected/unauthorized. The system 10 may then be configured to alert a family member, guardian, or healthcare professional of the unexpected/unauthorized usage. For example, a displacement by a second user of a health-related item 12 after a first user already displaced the same health-related item 12 within a pre-specified time period may indicate that the usage is unexpected/unauthorized and indicate that intervention is necessary by a family member, guardian, or healthcare professional.

Alternatively, the determination of the unexpected/unauthorized utilization may be based on identity of the user by comparing the identity of the user to a user database which includes one or more user assignments for each of the health-related items 12. The identity of the user may be based on biometrics, such as finger prints, voice recognition, iris scan, visual recognition, or combinations thereof. Further, the identity of the user may be based on authentications, such as pass codes, passwords, electronic keys, or combinations thereof. The system 10 may then be configured to alert a family member, guardian, or healthcare professional of the unexpected/unauthorized usage. For example, a displacement by a second user of a health-related item 12 assigned to only a first user may indicate that the usage is unexpected/unauthorized and indicate that intervention is necessary by a family member, guardian, or healthcare professional.

The system 10 may be further configured to generate a request for an appointment with a healthcare professional after a pre-specified usage threshold has been exceeded. The system 10 may be further configured to generate alerts regarding potential allergy restrictions of a user of the system 10 relating to the health-related items 12 or negative interactions between a user's medication and the health-related items 12. The system 10 may be further configured to generate alerts for a family member, caregiver, or guardian, after a pre-specified usage threshold has been exceeded.

In embodiments, the system 10 is configured to execute the instructions to receive, by the one or more data processors 20, the presence data of the health-related items 12 from a storage space (in certain embodiments, the container 14), receive, by the one or more data processors 20, status data of the health-related items 12 from a database, the status data includes recall data and expiration data for the health-related items 12, access, by one or more data processors 20, the reorder model 54 that generates the reorder signal in response to the presence data and the status data, and generate the reorder signal upon satisfying the pre-specified reorder threshold. In various embodiments, the storage space may be any space configured to store the health-related items 12 that is defined by "fencing" the health-related items 12 to a predetermined area utilizing the item presence sensor 16. Non-limiting examples of suitable storage spaces may include shelves, closets, bags, containers, vehicles, boxes, rooms, etc.

In embodiments, the system 10 is configured to execute the instructions to receive, by the one or more data processors 20, presence data of the health-related items 12 from the storage space (in certain embodiments, the container 14), receive, by the one or more data processors 20, geographic location data of the storage space from the database, access, by the one or more data processors 20, the tracking model 52 that generates the elevated-usage signal in response to the presence data and the geographic location data, and generate the elevated-usage signal upon satisfying the pre-specified usage threshold.

In embodiments, the system 10 is configured to execute the instructions to receive, by the one or more data processors 20, presence data of the health-related items 12 from the storage space (in certain embodiments, the container 14), access, by the one or more data processors 20, a tracking model that generates a reduced-usage signal in response to the presence data, and generate the reduced-usage signal upon satisfying a pre-specified usage threshold.

In embodiments, the system 10 is configured to execute the instructions to receive, by the one or more data processors 20, presence data of the health-related items 12 from the storage space (in certain embodiments, the container 14), access, by the one or more data processors 20, a tracking model that generates a unexpected/unauthorized-usage signal in response to the presence data, and generate the unexpected/unauthorized-usage signal upon satisfying a pre-specified usage threshold.

With reference to FIGS. 3 and 5-8, the system 10 may further include a computing device 38 configured to be utilized by the user. The computing device 38 may include smart phones, tablets, personal computers, wearables (e.g., smart watch, headset, and the like), smart hub (e.g., Amazon Echo, Google Home, and the like) and or combinations thereof. The computing device 38 may be configured to provide an operating system, such as Amazon Alexa, Microsoft Cortana, Google Assistant and Apple Siri. The system 10 may be configured to communicate with a cloud-based application for memorializing occurrences of aliments. Non-limiting examples of suitable cloud-based applications include calendars, Apple Health, or a combination thereof.

The computing device 38 may be separate from the container 14. Alternatively, the computing device 38 may be directly coupled to the container 14. The computing device 38 may be communicatively coupled to the container 14 and the server 36. Notifications generated by the system 10 may be received and accessible by the computing device 38. The system 10 may be configured to generate a graphical user interface 60 that can be displayed on the computing device 38, such as an inventory dashboard 62A (see FIG. 5), an inventory list 62B (see FIG. 6), or a product information page 62C (see FIG. 7), or configured to generate a graphical analysis 58 that can be displayed on the computing device 38, such as a heat map (see FIG. 8). In certain embodiments, the computing device 38 is configured to analyze the sensor tag 18 corresponding to the health-related items 12 to obtain information regarding the health-related items 12.

In embodiments, the system 10 may be configured to communicate with devices for the purpose of dosing/adjusting medication, such as a scale, a blood pressure determination device, a thermometer, a glucometer, air quality monitor, or combinations thereof. The system 10 may be configured to provide a preliminary diagnosis of an ailment and treatment recommendation utilizing the health-related items 12 by receiving information from a user, a device, or a combination thereof. The information received may be applied to a diagnosis model to generate a diagnosis data in response to the information. The diagnosis data may be applied to a treatment model and generate treatment data in response to the diagnosis data. The system 10 may be configured to provide instructions for usage of the health-related items 12 visually on a display or audibly by a speaker based on the diagnosis data.

In embodiments, the system 10 includes a messaging component configured to communicate with a healthcare professional or provider to assist in usage of the health-related items 12 within the container 14. Non-limiting examples of suitable messaging components include text messaging, voice communication, e-mail, push notifications, or combinations thereof. In certain embodiments, the system 10 is configured to generate and send a notification to Emergency medical services (EMS) in response to the use of certain health-related items 12 commonly utilized in an emergency, such as an ASA for heart attack or an EpiPen for anaphylactic attack.

In embodiments, the system 10 includes a pharmaceutical database including information regarding pharmaceuticals that possess incompatibilities with other pharmaceuticals and including information regarding the pharmaceuticals currently utilized by the user. The system 10 includes a pharmaceutical model configured to apply the heath-related items 12 to the pharmaceutical database and generate an incompatibility signal based on the pharmaceuticals currently utilized by the user.

In embodiments, the system 10 includes a form creation component, such as a "sick note" based on usage of the system 10.

In embodiments, the system 10 is configured to be "geo-fenced" within a certain location based on GPS, cellular triangulation, Wi-Fi connection, or combinations thereof. If the system 10, such as the container 14, is removed from the "geo-fence," the system 10 may generate a notification to a user regarding the current location of the container 14.

In embodiments, the system 10 includes a storage device 40 for storing instructions for maintaining the supply of health-related items 12. The instructions stored in the storage device 40 may include one or more separate programs, each of which includes an ordered listing of executable instructions for implementing logical functions. It is to be appreciated that while the executable instructions may be ordered, intervening executable instructions may be included between any two or more the executable instructions expressly described above. When the system 10 is in operation, the one or more data processors 20 are configured to execute the instructions stored within the storage device 40, to communicate data to and from the storage device 40, and to generally control operations of the system 10 pursuant to the instructions.

The system 10 may further includes a temperature sensor. The system 10 can monitor the temperature of the health-related items 12 or the compartments 28 to determine whether the health-related items 12 is or has been exposed to a temperature outside of the recommended temperature range by the manufacture of the health-related item 12.

The system 10 may further include a battery 42 with the battery 42 configured to energize the container 14. However, it is to be appreciated that the battery 42 may be configured to energize any component of the system 10. In certain embodiments, the container 14 includes the battery 42 disposed therein. However, it is to be appreciated that the battery 42 may be separate from the container 14.

The container may further include a data port 44. The data port 44 may be configured to electrically couple the battery 42 to the electrical grid for charging the battery 42, transmit information to the one or more data processors 20, or a combination thereof. In certain embodiments, the data port 44 is a USB port.

Figure 9:
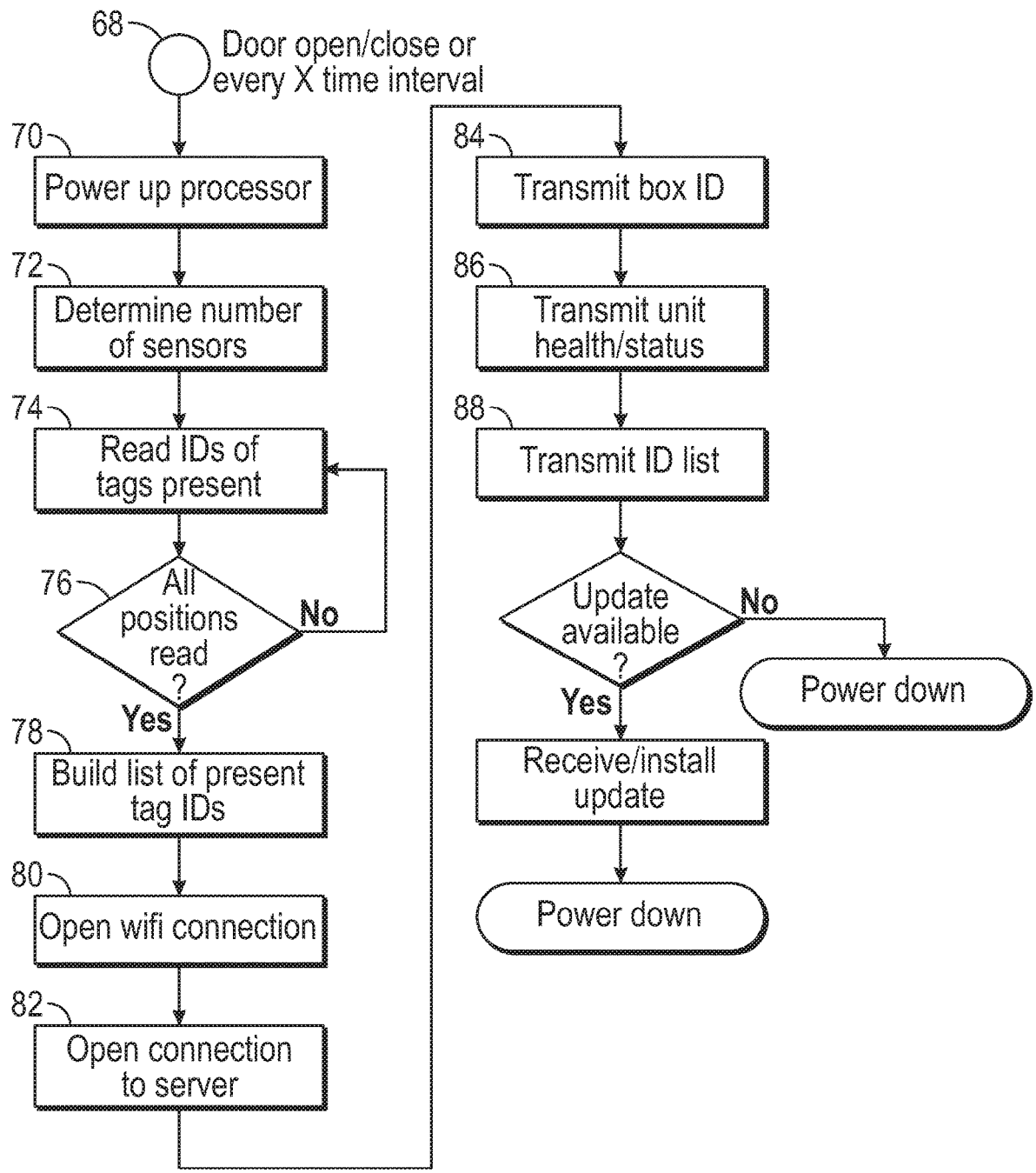
FIG. 9 is another flow chart illustrating a non-limiting embodiment of the system of FIG. 1.

With reference to FIG. 9, in exemplary embodiments, a method for maintaining a supply of a health-related item is provided herein. The method may include the step 68 of initiating the system 10. The system 10 may be initiated by opening and closing the cover 24 or after waiting the pre-specified interval of time. The method may further include the step 70 of powering up the one or more data processors 20. The method may further include the step 72 of determining the number of item presence sensors 16. The method may further include the step 74 of reading the UIDs of the sensor tags 18 by the item presence sensors 16. The method may further include the step 76 of determining whether all item presence sensors 16 attempted to read the UIDs of the sensor tags 18. The method may further include the step 78 of generating a list of the UIDs of the sensor tags 18 that were read by the item presence sensors 16. The method may further include the step 80 of establishing a communication connection (e.g., via Wi-Fi) from the container 14 to the server 36. The method may further include the step 82 of establishing a communication connection from the server 36 to the container 14. The method may further include the step 84 of transmitting the UID of the container 14 from the container 14 to the server 36 via the communication connection. The method may further include the step 86 of transmitting the health and status information (e.g., location, battery life, connection quality, etc.) of the container 14 from the container 14 to the server 36 via the communication connection. The method may further include the step 88 of transmitting the list of UIDs of the sensor tags 18 that were read by the item presence sensors 16 from the container 14 to the server 36 via the communication connection.

Figure 10:
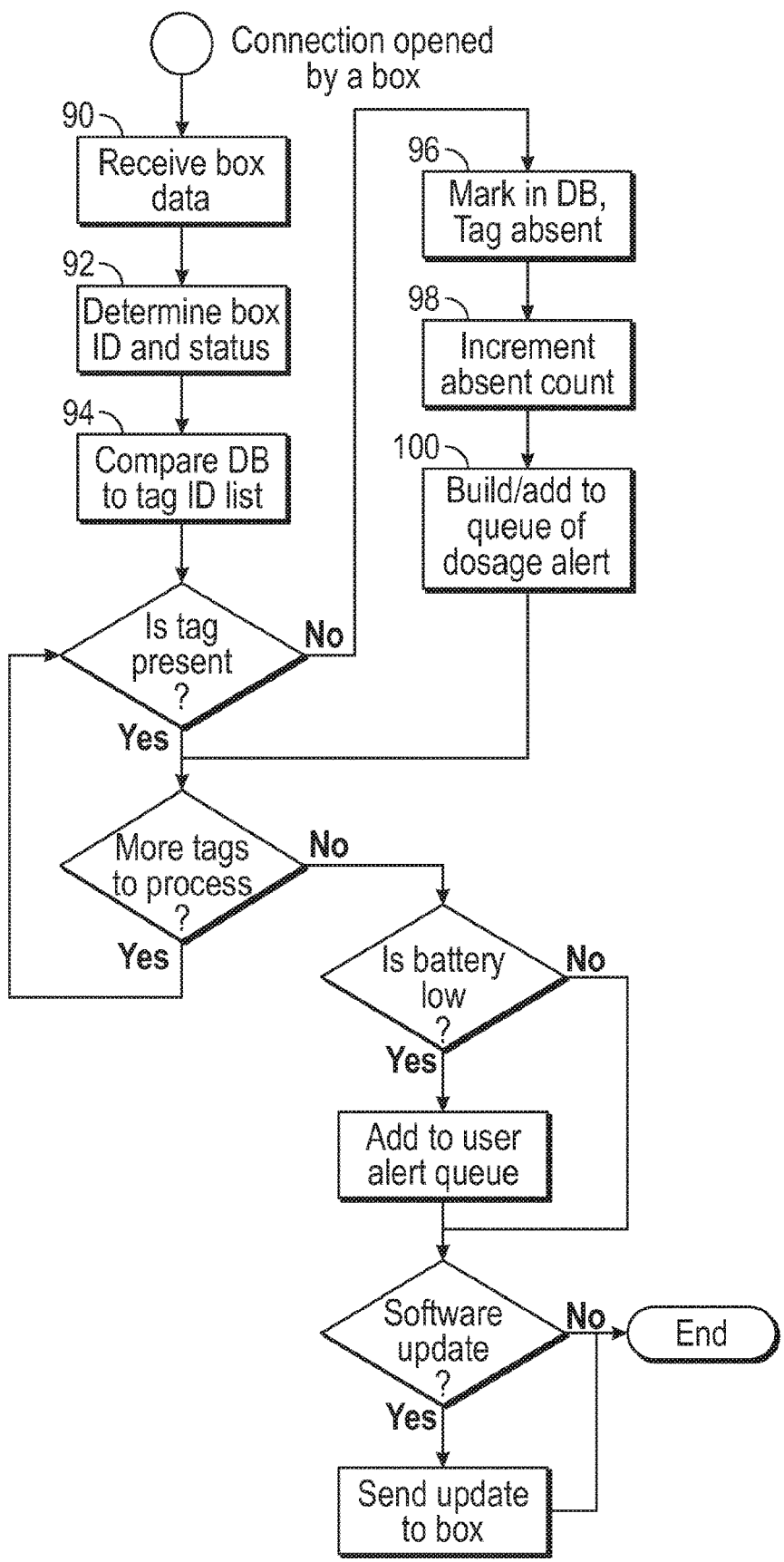
FIG. 10 is another flow chart illustrating a non-limiting embodiment of the system of FIG. 1.

With reference to FIG. 10, in exemplary embodiments, the method may further include the step 90 of receiving the list of UIDs of the sensor tags 18 that were read by the item presence sensors 16 from the container 14. The method may further include the step 92 of receiving the UID of the container 14 from the container 14 and the health and status information container 14. The method may further include the step 94 of comparing the list of UIDs of the sensor tags 18 that were read by the item presence sensors 16 to a database including supply information for the UID of the container 14 relating to the UIDs of the sensor tags 18 that are expected to be present in the container 14. The method may further include the step 96 of classifying the UIDs of the sensor tags 18 that are not present in the container 14 as "absent." The method may further include the step 98 of applying the count of "absent" classifications for each UID of the sensor tags 18 to the pre-specified reorder threshold. The method may further include the step 100 of adding the UIDs of the sensor tags 18 that exceed the pre-specified reorder threshold to a reorder database.

Figure 11:
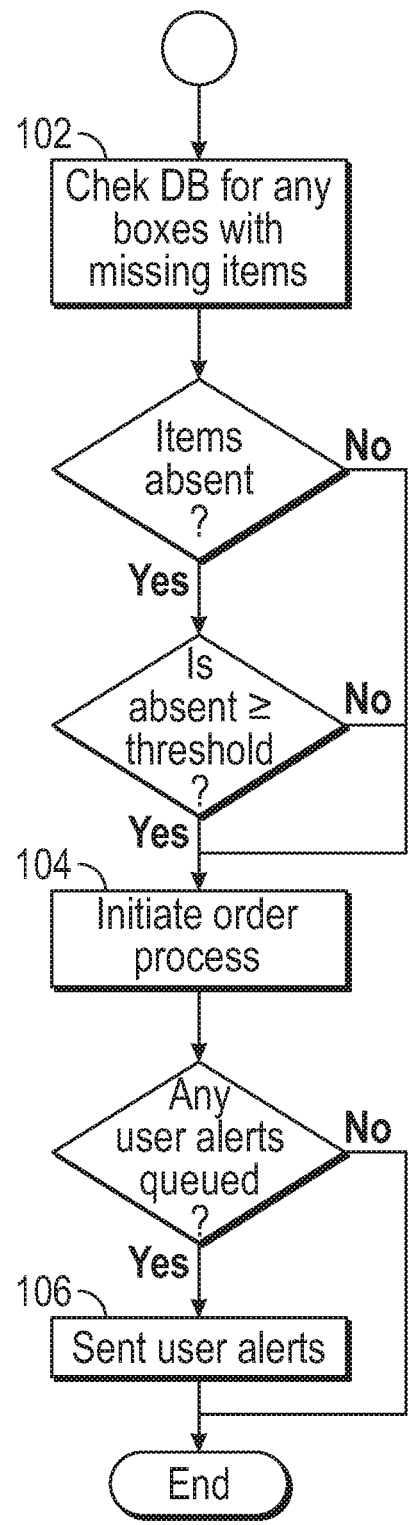
FIG. 11 is another flow chart illustrating a non-limiting embodiment of the system of FIG. 1.

With reference to FIG. 11, in exemplary embodiments, the method may further include the step 102 of determining whether any UIDs are included in the reorder list. The method may further include the step 104 of initiating an order process for the health-related items 12 corresponding to the UIDs included in the reorder list. The method may further include the step 106 of generating an alert regarding the health-related items 12 corresponding to the UIDs included in the reorder list, transmitting the alert to the computing devices 38, and displaying or announcing the alert on the computing devices 38.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration in any way. Rather, the foregoing detailed description will provide those skilled in the art with a convenient road map for implementing an exemplary embodiment, it being understood that various changes may be made in the function and arrangement of elements described in an exemplary embodiment without departing from the scope as set forth in the appended claims and their legal equivalents.

What is claimed is:

1. A processor-implemented system for tracking usage of a supply of a health-related items, the system comprising:
   a storage device for storing instructions for tracking usage of the supply of the health-related item; and
   one or more data processors configured to execute the instructions to:
      receive, by one or more data processors, presence data of the health-related item from a storage space, the storage space comprises an item presence sensor configured to determine whether the health-related item is present within the storage space;
      receive, by one or more data processors, geographic location data of the storage space from a database;
      access, by one or more data processors, a tracking model that generates an elevated-usage signal in response to the presence data and the geographic location data, the model comprises a pre-specified usage threshold; and
      generate the elevated-usage signal upon satisfying the pre-specified usage threshold.

2. The processor-implemented system of claim 1, wherein the storage space comprises a container, the container comprises a housing and a cover pivotably coupled to the housing, the housing comprises a compartment, and the compartment is configured to store the health-related item.

3. The processor-implemented system of claim 2, wherein the container comprises a first cover and a second cover, the first cover and the second cover are opposite each other relative to the housing, the housing comprises a first compartment facing the first cover and a second compartment facing the second cover, and the item presence sensor is disposed between the first compartment and the second compartment.

* * * * *